US006741880B1

United States Patent (10) Patent No.: US 6,741,880 B1
Foo et al. (45) Date of Patent: *May 25, 2004

(54) METHOD AND APPARATUS FOR EFFICIENT STENOSIS IDENTIFICATION AND ASSESSMENT USING MR IMAGING

(75) Inventors: Thomas K. F. Foo, Rockville, MD (US); Vincent B. Ho, North Bethesda, MD (US); Manojkumar Saranathan, Rockville, MD (US)

(73) Assignee: General Electric Company, Schenectady, NY (US)

( * ) Notice: Subject to any disclaimer, the term of this patent is extended or adjusted under 35 U.S.C. 154(b) by 340 days.

This patent is subject to a terminal disclaimer.

(21) Appl. No.: 09/595,117

(22) Filed: Jun. 16, 2000

(51) Int. Cl.[7] ................................................. A61B 5/05
(52) U.S. Cl. ........................ 600/419; 600/407; 600/410; 600/420; 382/128; 324/300; 324/307
(58) Field of Search ................................. 600/410, 419, 600/420, 407; 382/128; 324/300, 307

(56) References Cited

U.S. PATENT DOCUMENTS 6,317,620 B1 * 11/2001 Ho et al. ..................... 324/306
6,408,201 B1 *  6/2002 Foo et al. .................... 324/300

OTHER PUBLICATIONS

Moran PR. A flow velocity zeugmatographic interlace for NMR imaging in humans. *Magnetic Resonance Imaging* 1982; 1: 197–203.
Bryant DJ, Payne JA, Firmin DN, and Longmore DB. Measurement of flow with NMR imaging using a gradient pulse and phase difference technique. *J. Comput Assist Tomogr* 1984; 8: 588–93.
van Dijk P. Direct cardiac NMR imaging of heart wall and blood flow velocity. *J. Comput Assist Tomogr* 1984; 8: 429–36.
Nayler GL, Firmin DN, and Longmore DB. Blood flow imaging by cine magnetic resonance. *J. Comput Assist Tomogr* 1986; 10: 715–22.
Swan JS, Grist TM, Weber DM, Sproat IA, and Wojtowycz MM. MR angiography of the pelvis with variable velocity encoding and a phase–array coil. *Radiology* 1994; 190: 363–9.
Swan JS, Weber DM, Grist TM, Wojtowycz MM, Korosec FR, and Mistretta CA. Peripheral MR angiography with variable velocity encoding. Work in progress. *Radiology* 1992; 184: 813–7.

(List continued on next page.)

Primary Examiner—Angela D. Sykes
Assistant Examiner—William C. Jung
(74) Attorney, Agent, or Firm—Ziolkowski Patent Solutions Group, LLC; Michael A. Della Penna; Carl B. Horton

(57) ABSTRACT

A method and apparatus is disclosed in which a two-tiered approach is taken to first grade a patient to identify the presence of any suspected stenosis, and then a second step is used to acquire more detailed information to grade the stenosis. The invention includes performing a screening study by acquiring a first MR image having a low resolution to scan a suspected stenosis region. After analyzing the first MR image to identify a suspected stenosis within the suspected stenosis region, a more detailed study is performed by acquiring a second MR image having a higher resolution than the first MR image to scan the identified suspected stenosis. If no lesions, or stenotic vessels, are identified after the first MR image, the second MR image need not be obtained. Since the first MR image is designed to be more sensitive to the detection of such stenosis, by increasing the conspicuity of the lesions, and using a fast acquisition sequence, this two-tiered approach increases the efficiency for accurate coronary artery stenosis detection and assessment.

31 Claims, 3 Drawing Sheets

OTHER PUBLICATIONS

Ehman RL, Felmlee JP. Adaptive technique for high definition MR imaging of moving structures. *Radiology* 1998; 173: 255–263.

Ho KY, Leiner T, de Haan MW, Kessels AG, Kitslaar PJ, and van Engelshoven JM. Peripheral vasculature tree stenoses: evaluation with moving–bed infusion–tracking MR angiography. *Radiology* 1998; 206: 683–92.

Meaney JF, Ridgway JP, Chakraverty S, Robertson I, Kessel D, Radjenovic A, Kouwenhoven M, Kassner A, and Smith MA. Stepping–table gadolinium–enhanced digital substraction MR angiography of the aorta and lower extremity arteries: preliminary experience. *Radiology* 1999; 211: 59–67.

Foo, TKF, Saranathan M, Prince MR, and Chenevert TL. Automated detection of bolus arrival and initiation of data acquisition in fast, three–dimensional, gadolinium–enhanced MR angiography. *Radiology* 1997; 203: 275–80.

Wilman AH, Riederer SJ, Huston J. $3^{rd}$, Wald JT, and Debbins JP. Arterial phase carotid and vertebral artery imaging in 3D contrast–enhanced angiography by combining fluroscopic triggering with an elliptical centric acquisition order. *Magn. Reson Med.* 1998; 40: 24–35.

Riederer SJ, Fain SB, Kruger DG, and Busse RF. 3D contrast–enhanced MR angiography using fluoroscopic triggering and an elliptical centric view order. *Int. J. Card Imaging* 1999; 15: 117–29.

* cited by examiner

METHOD AND APPARATUS FOR EFFICIENT STENOSIS IDENTIFICATION AND ASSESSMENT USING MR IMAGING

BACKGROUND OF THE INVENTION

The present invention relates generally to the art of locating a blood vessel lesion in a human subject, and more particularly, to an apparatus and method to efficiently identify a lesion and grade the stenosis using magnetic resonance imaging (MRI) technology.

The narrowing or constriction of vessels carrying blood to the heart is a well-known cause of heart attacks, and gone untreated, can lead to sudden death. In such stenotic vessels, it is known that the flow in the vessel at the point of narrowing and immediately after the narrowing is characterized by rapid flow velocities and/or complex flow patterns. In general, narrowing of blood carrying vessels supplying an organ will ultimately lead to compromised function of the organ in question, at best, and organ failure at worst. Quantitative flow-velocity data can readily aid in the diagnosis and management of patients and also help in the basic understanding of disease processes. There are many techniques available for the measurement of regional blood flow to a specific region of the anatomy, including imaging based methods using radiographic imaging of contrast agents, both in projection and computed tomography (CT), ultrasound, and nuclear medicine techniques. Radiographic and nuclear medicine techniques require the use of ionizing radiation and/or contrast agents. However, none of these techniques provide instantaneous flow-velocity measurements at a specific spatial location and/or specific time in the cardiac cycle. Two methods that are in current use are doppler ultrasound using an external transducer or the more invasive method of an intra-vascular doppler ultrasound guide-wire/probe.

The functional significance of a stenosis is conventionally determined using Doppler ultrasound to measure the velocity/pressure gradient across the vessel constriction along the axis of flow. The higher the gradient, the more significant the stenosis. However, using Doppler ultrasound is dependent on having an acoustic window allowing the ultrasound beam to insonify the vessel of interest at an angle of incidence as close to zero (i.e., parallel to the vessel) as possible. Furthermore, Doppler ultrasound does not provide the quality of images that are produced using MR technology. Further, ultrasound techniques are difficult to apply in certain situations because of intervening tissues such as bone, excessive fat or air. The use of an intra-vascular doppler ultrasound probe avoids some of these pitfalls but the procedure is quite invasive and has an associated risk of patient morbidity.

Phase contrast magnetic resonance angiography (MRA) is a practical and clinically applicable technique for imaging blood flow-velocities. MRI utilizes radio frequency pulses and magnetic field gradients applied to a subject in a strong magnetic field to produce viewable images. When a substance containing nuclei with net nuclear magnetic moment, such as the protons in human tissue, is subjected to a uniform magnetic field (polarizing field $B_0$), the individual magnetic moments of the spins in the tissue attempt to align with this polarizing field (assumed to be in the z-direction), but precess about the direction of this magnetic field at a characteristic frequency known as the Larmor frequency. If the substance, or tissue, is subjected to a time-varying magnetic field (excitation field $B_1$) applied at a frequency equal to the Larmor frequency, the net aligned moment, or "longitudinal magnetization", $M_Z$, may be nutated, or "tipped", into the x-y plane to produce a net transverse magnetic moment $M_t$. A signal is emitted by the excited spins after the excitation signal $B_1$ is terminated (as the excited spins decays to the ground state) and this signal may be received and processed to form an image.

When utilizing these signals to produce images, magnetic field gradients ($G_x$, $G_y$ and $G_z$) are employed. Typically, the region to be imaged is scanned by a sequence of measurement cycles in which these gradients vary according to the particular localization method being used. The resulting MR signals are digitized and processed to reconstruct the image using one of many well-known reconstruction techniques.

Phase contrast MRA makes use of flow encoding gradient pulses which impart a velocity-dependent phase shift to the transverse magnetization of moving spins while leaving stationary spins unaffected (Moran P. R. A Flow Velocity Zeugmatographic Interlace for NMR Imaging in Humans. Magnetic Resonance Imaging 1982; 1: 197–203). Each phase contrast acquisition generates two images: a magnitude image that is proportional to the proton density of the object and may also be $T_1$-weighted, and an image representing the phase of the object. The phase image produced has information only from the moving spins and the signal from stationary tissue is suppressed. Images representing both the average flow-velocity over the entire cardiac cycle and at a series of individual points in the cycle have been generated using this technique. The phase contrast MR method produces phase images with intensities that represent the magnitude of the flow velocity and also the direction of flow. Therefore, such images may be used for both qualitative observation of blood flow and quantitative measurement. The practical application of phase contrast MR angiography and venography to the quantitative determination of flow velocity is therefore evident.

It would also be advantageous to use magnetic resonance imaging technology to efficiently locate and identify a stenosis in a blood vessel and use this MR technology to grade the stenosis for patient management decisions. Previous attempts at using MR technology to improve the ability to detect and grade coronary artery stenosis, for example, have relied primarily on using a single scan and decreasing the intra-voxel flow dephasing effects by decreasing pixel size, together with using first moment gradient nulling for flow compensation, and decreasing echo time (TE). It would be desirable to improve on this prior art by accomplishing the converse. That is, it would be advantageous to increase the intra-voxel flow dephasing effects to exacerbate flow voids, and therefore increase the conspicuity of lesions on the coronary artery that result in a stenosis in a quick screening exam. It would also be advantageous to have a method and apparatus for efficient visualization of a stenosis using MR technology followed with a more thorough exam if a stenosis is detected initially.

SUMMARY OF THE INVENTION

The present invention relates to a method and apparatus for efficient stenosis identification and assessment using MR technology, that solves the aforementioned problems.

The present invention includes a two step approach to accurately identify a blood vessel lesion and specify the degree of stenosis. In the initial step, an examination for lesion identification is disclosed using a low spatial resolution MR image. Preferably, the MR image is acquired using a gradient echo imaging pulse sequence with a flow sensitive bi-polar gradient waveform. The bi-polar gradients generate a broad distribution of velocities in a large voxel. Since a stenosis present in a given voxel will result in intra-voxel flow dephasing in voxels immediate to and distal to the stenosis, the stenosis can be quickly and efficiently localized using the initial step. After the stenosis is identified, a second step is performed in which a high spatial resolution MR image is acquired for more accurate and specific grading of the stenosis in the targeted area.

According to one aspect of the invention, a method of identifying a stenotic vessel using MR imaging is disclosed which includes performing a screening study by acquiring a first MR image having a low resolution to scan a suspected stenosis region. The method next includes analyzing the first MR image to identify a suspected stenosis within the suspected stenosis region, then performing a detailed study by acquiring a second MR image having a higher resolution than the first MR image, to scan the identified suspected stenosis. Next, the second MR image is analyzed to identify and/or grade an actual stenosis.

In accordance with another aspect of the invention, an examination method is disclosed to identify a lesion in a blood vessel and grade a stenosis resulting therefrom. The examination includes acquiring a first MR image using a gradient echo imaging pulse sequence having a flow sensitizing bi-polar gradient waveform, and detecting and localizing a suspected stenosis using the first MR image. The method next involves acquiring a second MR image if a stenosis is detected and localized. The second MR image has a higher resolution than the first MR image and is acquired in a region in which the suspected stenosis is detected and localized to grade the suspected stenosis. If a stenosis is not detected and localized, the examination is ended without further MR image acquisitions.

In accordance with another aspect of the invention, an MRI apparatus is disclosed to conduct MR stenosis screening, and if necessary, grade a stenotic vessel that includes an MRI system having a number of gradient coils positioned about a bore of a magnet to impress a polarizing magnetic field, an RF transceiver system, and an RF modulator controlled by a pulse control module to transmit RF signals to an RF coil assembly in order to acquire MR images. The MRI apparatus also includes a computer programmed to operate the MRI system in two modes of operation to efficiently conduct a stenosis exam. The first mode is programmed to acquire at least one first MR image with low resolution over a relatively large region, then allow a user to analyze the at least one first MR image for an indication of a stenosis. The first mode of operation also includes receiving input to either end the stenosis exam or switch to the second mode of operation. In the second mode of operation, the computer is programmed to create a localized region of the relatively large region in order to target a suspected stenosis, and then acquire at least one second MR image with resolution higher than that of the at least one first MR image of the localized region.

In accordance with yet another aspect of the invention, the aforementioned methods are implemented in a computer program that is fixed on a computer readable storage medium that, when executed, causes the computer to acquire a first MR image of a relatively large region. The first MR image has high phase cancellation/intra-voxel dephasing in the immediate vicinity of a stenosis to screen a patient for possible arterial lesions. The computer is further programmed to limit a field-of-view (FOV) to a target region within the relatively large region if a possible arterial lesion is identified, and then acquire a second MR image of the targeted region. The second MR image having a resolution higher than that of the first MR image, and only being acquired if the first MR image indicates the presence of a lesion or stenosis.

In this manner, the higher resolution targeted acquisition near the site of interest is performed only if a lesion is present to effectively grade the stenosis. This technique provides a two-step technique involving a first step with increased sensitivity to detect lesions that can be acquired quickly, and then only performing the more time-consuming second step of acquiring an image with high specificity for grading the lesion only if one is detected in the first step. This two-tiered approach increases the efficiency for accurate coronary artery stenosis detection and assessment.

Various other features, objects and advantages of the present invention will be made apparent from the following detailed description and the drawings.

BRIEF DESCRIPTION OF THE DRAWINGS

The drawings illustrate the best mode presently contemplated for carrying out the invention.

In the drawings.

DETAILED DESCRIPTION OF THE PREFERRED EMBODIMENT

Figure 1:
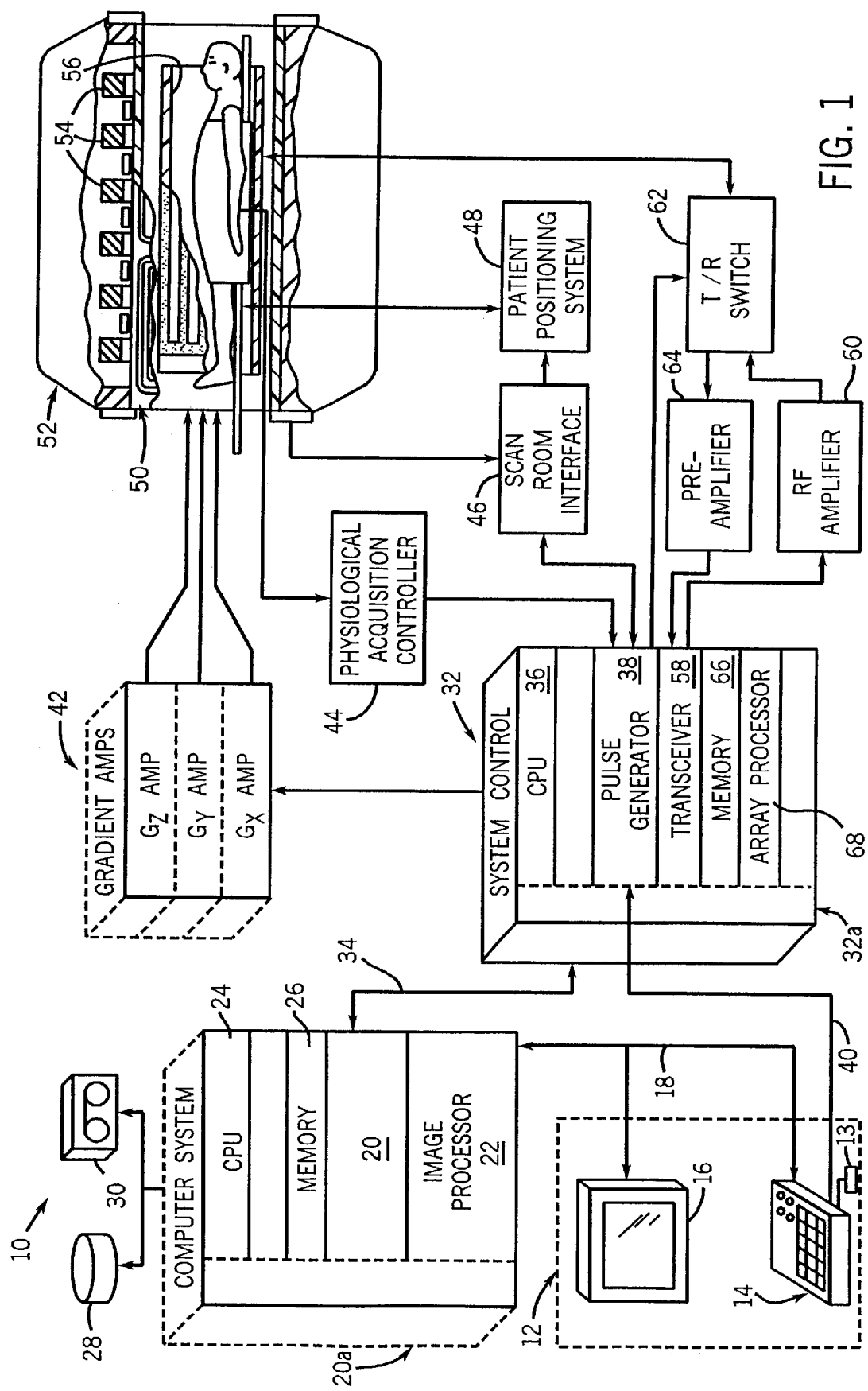
FIG. 1 is a schematic block diagram of an NMR imaging system for use with the present invention.

Referring to FIG. 1, the major components of a preferred MRI system 10 incorporating the present invention are shown. The operation of the system is controlled from an operator console 12 which includes a keyboard or other input device 13, a control panel 14, and a display 16. The console 12 communicates through a link 18 with a separate computer system 20 that enables an operator to control the production and display of images on the screen 16. The computer system 20 includes a number of modules which communicate with each other through a backplane 20a. These include an image processor module 22, a CPU module 24 and a memory module 26, known in the art as a frame buffer for storing image data arrays. The computer system 20 is linked to a disk storage 28, a tape drive 30, or any other form of computer readable storage medium for storage of image data and programs, and it communicates with a separate system control 32 through a high speed serial link 34. The input device 13 can include a mouse, joystick, keyboard, track ball, touch screen, light wand, voice control, or similar device, and may be used for interactive geometry prescription.

The system control 32 includes a set of modules connected together by a backplane 32a. These include a CPU module 36 and a pulse generator module 38 which connects to the operator console 12 through a serial link 40. It is through link 40 that the system control 32 receives commands from the operator which indicate the scan sequence that is to be performed. The pulse generator module 38 operates the system components to carry out the desired scan sequence and produces data which indicates the timing, strength and shape of the RF pulses produced, and the timing and length of the data acquisition window. The pulse generator module 38 connects to a set of gradient amplifiers 42, to indicate the timing and shape of the gradient pulses that are produced during the scan. The pulse generator module 38 also receives patient data from a physiological acquisition controller 44 that receives signals from a number of different sensors connected to the patient, such as ECG signals from electrodes attached to the patient. The pulse generator module 38 connects to a scan room interface circuit 46 which receives signals from various sensors associated with the condition of the patient and the magnet system. It is also through the scan room interface circuit 46 that a patient positioning system 48 receives commands to move the patient to the desired position for the scan.

The gradient waveforms produced by the pulse generator module 38 are applied to the gradient amplifier system 42 having $G_x$, $G_y$, and $G_z$ amplifiers. Each gradient amplifier excites a corresponding gradient coil in an assembly generally designated 50 to produce the magnetic field gradients used for spatially encoding acquired signals. The gradient coil assembly 50 forms part of a magnet assembly 52 which includes a polarizing magnet 54 and a whole-body RF coil 56. A transceiver module 58 in the system control 32 produces pulses which are amplified by an RF amplifier 60 and coupled to the RF coil 56 by a transmit/receive switch 62. The resulting signals emitted by the excited nuclei in the patient may be sensed by the same RF coil 56 and coupled through the transmit/receive switch 62 to a preamplifier 64. The amplified MR signals are demodulated, filtered, and digitized in the receiver section of the transceiver 58. The transmit/receive switch 62 is controlled by a signal from the pulse generator module 38 to electrically connect the RF amplifier 60 to the coil 56 during the transmit mode and to connect the preamplifier 64 during the receive mode. The transmit/receive switch 62 also enables a separate RF coil (for example, a surface coil) to be used in either the transmit or receive mode.

The MR signals picked up by the RF coil 56 are digitized by the transceiver module 58 and transferred to a memory module 66 in the system control 32. When a scan is completed, an array of raw k-space data has been acquired in the memory module 66. This raw k-space data is rearranged into separate k-space data arrays for each image to be reconstructed, and each of these is input to an array processor 68 which operates to Fourier transform the data into an array of image data. This image data is conveyed through the serial link 34 to the computer system 20 where it is stored in the disk memory 28. In response to commands received from the operator console 12, this image data may be archived on the tape drive 30, or it may be further processed by the image processor 22 and conveyed to the operator console 12 and presented on the display 16.

The present invention includes a method and system suitable for use with the above-referenced MR system, or any similar or equivalent system for obtaining MR images. The present invention is a two-tiered technique to improve the efficiency for accurate coronary artery stenosis identification and grading.

Figure 2:
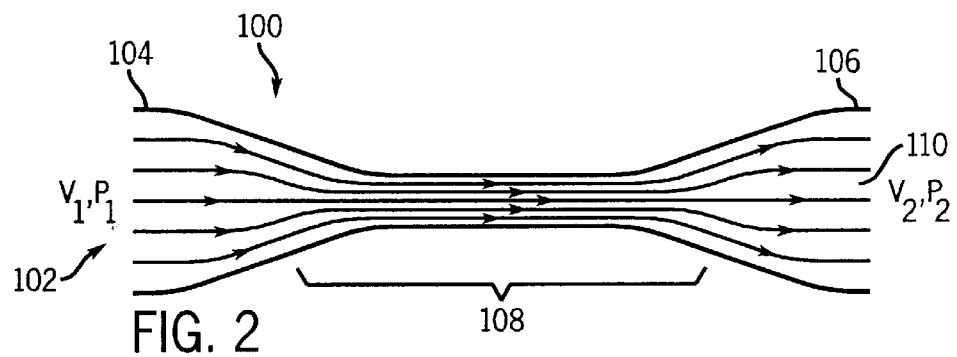
FIG. 2 is a schematic representation of an exemplary stenotic vessel in a human patient for which the present invention is directed at locating.

Referring to FIG. 2, a schematic representation of a blood vessel 100 is shown longitudinally with viscous blood 102 flowing therethrough. The blood vessel 100 is shown with a first end 104 acting as an inlet, and a second end 106 acting as an outlet. Between ends 104 and 106 is a constriction, or a stenotic area 108. In such a stenotic vessel, blood flow velocity $V_2$ at the outlet end 106 is greater than the blood flow velocity $V_1$ at the inlet at 104 (i.e., $V_2 > V_1$), and, correspondingly, the blood pressure $P_2$ at the outlet end 106 is less than the blood pressure $P_1$ at the inlet end 104 (i.e., $P_2 < P_1$). In general, in a stenotic vessel, such as blood vessel 100, the region 110 within the outlet end of the vessel 106, which is immediately downstream from the constriction 108, is characterized by having rapid blood flow velocities, or complex blood flow patterns. Furthermore, in regions where the degree of constriction is high, the emerging flow patterns in region 110 cease to be laminar and take on complex flow patterns, including the generation of flow vortices or eddys.

The present invention takes advantage of the fact that hemodynamically significant stenoses can be characterized by the high velocity gradients across the flow axis, and along its length. The hemodynamic severity of the stenosis can then be graded by the changes in the velocity gradients through the stenotic area. In general, the present invention is a two-tiered approach to identifying a stenotic vessel, or a region having a lesion on a blood vessel, then if needed, grading the stenosis with a more detailed image acquisition. This approach increases the efficiency for accurate stenosis detection and assessment in that by first acquiring a low resolution image (e.g., 1–2 mm. pixel) that is highly sensitive to lesion detection, a larger region can be initially scanned quickly, and if a lesion is identified, a second scan of higher resolution can be acquired for more accurate and specific grading of the stenosis.

Figure 3:
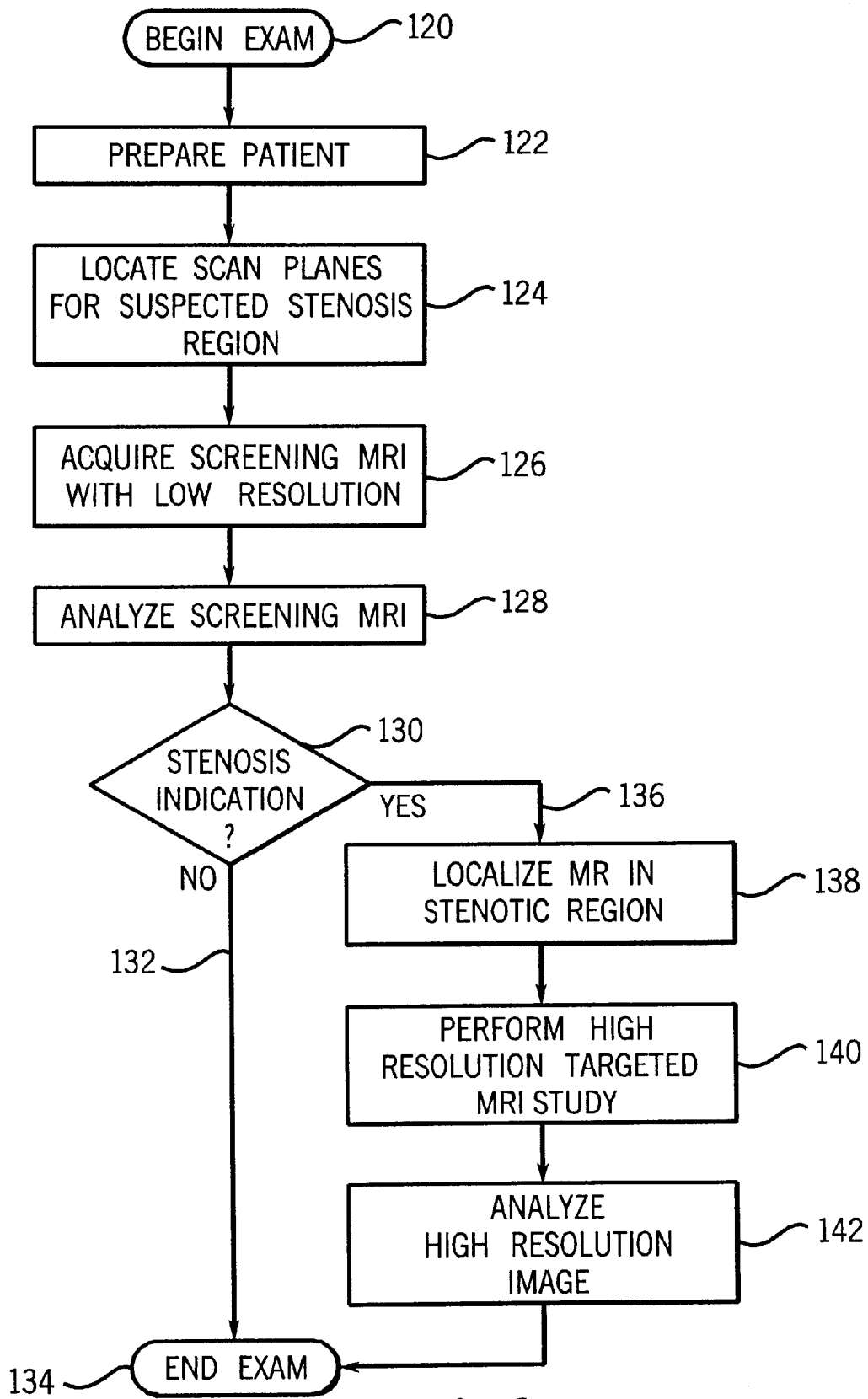
FIG. 3 is a flow chart illustrating an embodiment of the present invention.

FIG. 3 is a flow chart showing a preferred embodiment of the present invention that depicts both the method and a representation of the software programmed into the computer of the MRI apparatus of FIG. 1. The scan begins with an initialization 120 that includes patient preparation 122 to undergo an MRI exam, and is well known. The scan planes for a suspected stenosis are located 124, which typically would be the coronary arteries. A first MR image having low resolution is acquired to screen the scan planes 126. The first MR image is acquired using a pulse sequence with flow sensitizing bi-polar gradients, as will be further described with reference to FIG. 4. The first MR image is then analyzed at 128 for an indication of a lesion, or a stenosis, by looking for flow voids as an indication of the stenosis. The flow voids are generated close to or around the site of a stenosis as a result of applying the flow sensitizing bi-polar gradient waveform in all three directions in the pulse sequence. If there are no indications of flow voids 130, 132, and therefore, no indication of a stenosis, the exam is considered completed 134, and the patient released without further time-consuming MR image acquisitions. In this manner, patients can be more efficiently screened for coronary artery stenosis.

However, if a stenosis is indicated 130, 136, by the appearance of flow voids in the first MR image, the field-of-view (FOV) is limited to a target region of the suspected stenosis 138. Next, a second MR image is acquired having a higher resolution than the first MR image to scan the identified suspected stenosis within the targeted, localized region 140. The high spatial resolution image is then analyzed 142 to grade the stenosis, after which, the exam is complete 134. This then provides a method and system for increasing the sensitivity to detect lesions, and also a method and system that has high specificity for grading a lesion, not with a single acquisition, but with a series of acquisitions.

Figure 4:
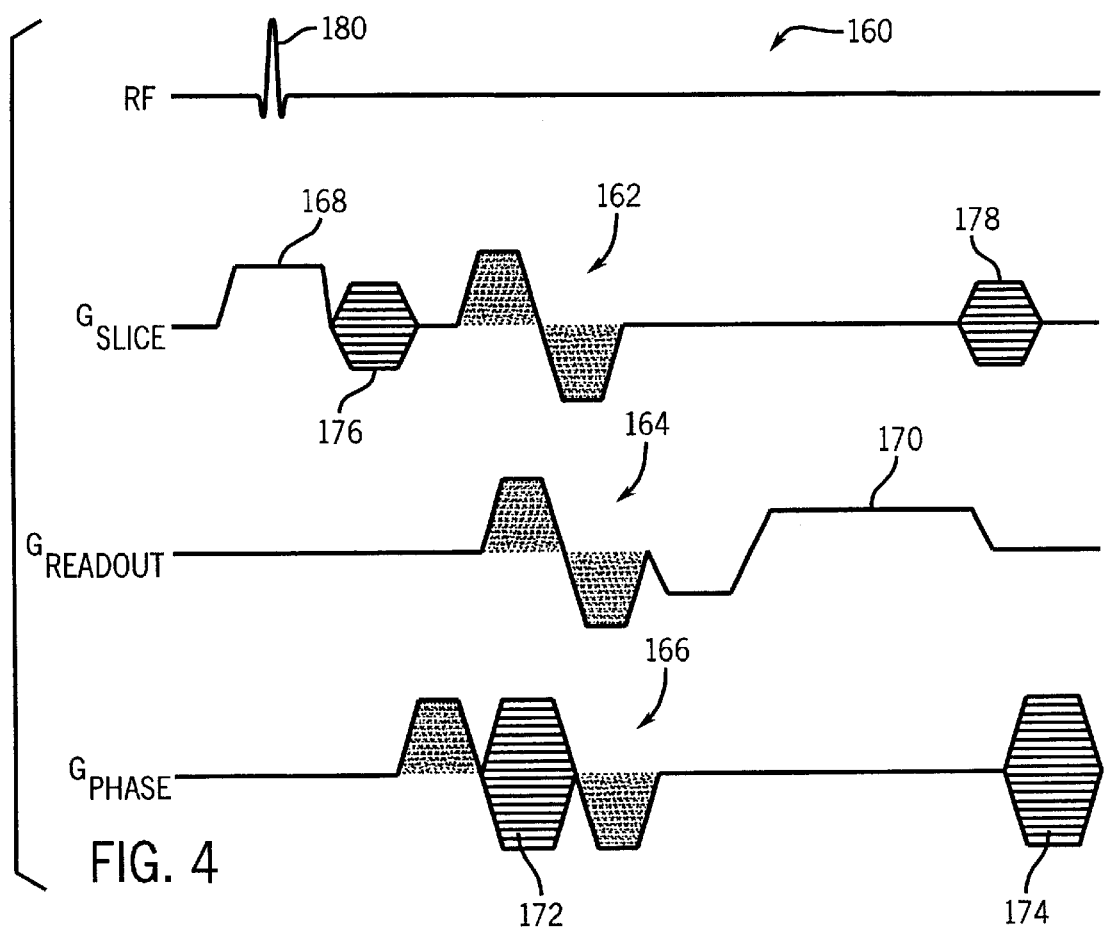
FIG. 4 is a timing diagram of a three-dimensional MR imaging pulse sequence used in the invention.

FIG. 4 shows the three-dimensional imaging pulse sequence 160 used in the present invention. Note that the method described is also applicable to two-dimensional pulse sequences as well. As shown in this preferred embodiment, the flow sensitizing gradients 162, 164, and 166 create a flow sensitive pulse sequence that behaves as a screening tool with high sensitivity to the detection of lesions. The flow sensitizing gradients 162, 164, and 166 are bi-polar gradients to accentuate phase cancellation and thereby increase flow dephasing. Alternatively, the flow dephasing in the first MR image can be accomplished by increasing the voxel size for greater distribution of the velocity vectors. In either case, the first (screening) MR image is acquired with high phase cancellation and low resolution, and therefore is acquired relatively fast. Generally, the first screening study can be accomplished with either a flow sensitive pulse sequence, as shown in FIG. 4, or with a contrast material enhanced imaging pulse sequence. The pulse sequence can be either a two-dimensional breath-held acquisition or a three-dimensional free-breathing acquisition that is respiratory-gated using a navigator echo, or similar respiratory gating technique.

Preferably, as shown in FIG. 4, the flow sensitizing bi-polar gradients 162, 164, and 166 are applied in all three directions to provide insensitivity to orientation of the blood vessel, or the stenosis. It is understood that although FIG. 4 shows the flow sensitizing gradients substantially aligned, since the present invention is not directed to measuring flow velocity, they need not be coincident. It is merely preferred that the flow sensitizing gradients 162, 164, and 166 be located between the pulse encoding gradient 168 and the readout gradient 170. The phase encoding gradients 172 and 174, along with the gradient crushers 176, 178 and the RF pulse 180 are each shown as reference points. Although the flow sensitizing gradient 166 in the phase direction is shown separated by the phase encoding gradient 172, it is understood that this is a preferred embodiment to increase flow sensitivity. Alternatively, each pole of the bi-polar gradient 166 can be brought closer together in time with a corresponding increase in amplitude of the first moment. As will become apparent, either a larger moment, or an increased temporal separation is needed to dephase the spins and increase flow sensitivity. In a preferred embodiment, the pulse sequence is a three-dimensional fast gradient echo pulse sequence using the bi-polar, flow sensitizing gradients 162, 164, 166.

The value of the first moment of the bi-polar gradient is nominally set to a low velocity encoded (VENC) value so that the velocity distribution within a voxel is greater than $2\pi$. This results in a cancellation of signal from that voxel as the net magnetization averages to zero, or close to zero.

Next, a brief summary description of the VENC value calculation and setting is explained. The value of the first moment for a single bi-polar gradient waveform is given by:

$$M_1 = AT,\quad [1]$$

where A is the area of the uni-polar part of a bi-polar gradient waveform, and T is the temporal separation between the two uni-polar lobes, each having opposite polarity, that constitute the bi-polar gradient waveform, as shown in FIG. 4. The resulting phase generated by the bi-polar gradient waveform is given by:

$$\phi = \gamma M_1 \vec{v} \quad [2]$$

where $\gamma$ is the gyromagnetic ratio and $\vec{v}$ is the velocity. The phase that is measured in phase-difference processing is given by: <needs to be $\Delta\phi$>

$$\Delta\phi = 2\gamma M_1 \vec{v}. \quad [3]$$

According to the present invention however, since the VENC value is such that at that particular velocity, the corresponding phase shift is $\pi$ radians, the first moment of the bi-polar waveform is adjusted such that:

$$M_1 = \frac{\pi}{\gamma VENC}. \quad [4]$$

As is evident from comparing Eqns. 3 and 4, this expression for the VENC value is one-half that used in a phase contrast acquisition where the phase difference between two acquisitions, with toggled polarity of the bi-polar waveforms, determines the value for the first moment.

The following description is a more complete explanation of bi-polar gradients. Considering a magnetic field gradient applied in a specific direction, the phase accumulated by a spin ensemble is a function of the equation of motion of that ensemble and the applied gradient field. That is:

$$\phi = \int_0^t \gamma \vec{G}(t) \cdot \vec{r}(t) dt, \quad [5]$$

where $\vec{G}(t)$ is the vector describing the time-varying gradient (direction and amplitude), and $\vec{r}(t)$ is the motion vector such that $$\vec{r}(t) = \vec{r}_0 + \vec{v}t + \tfrac{1}{2}\vec{a}t^2 + \ldots, \quad [6]$$

with the first term representing the initial position of the spin ensemble at time t=0 and the other terms representing the motion due to a constant velocity, acceleration, and the higher orders of motion. The higher orders of motion can be ignored for this description since the constant velocity component predominates.

To have a better understanding of the interaction of velocity and phase, Eqn. [5] can be expanded as:

$$\phi = \gamma r_0 \int_0^t G(t)dt + \gamma v \int_0^t tG(t)dt \quad [7]$$
$$= \gamma r_0 M_0 + \gamma v M_1,$$

where $M_0$ and $M_1$ represent the zeroth and first gradient moments, respectively. If G(t) is a single, uni-polar gradient lobe, the phase in a volume element would be given by Eqn.[7]. If, immediately following this gradient, an identical uni-polar gradient is applied with opposite sign, the phase due to this second gradient lobe is given by:

$$\phi' = \gamma r_0 M'_0 + \gamma M'_1. \quad [8]$$

Since the zeroth moment is merely the area under the gradient lobe, $M'_0$ is equal to $-M_0$. When combined, the two uni-polar lobes of identical area, but of opposite sign, are essentially a single bipolar gradient waveform. However, as the first moment is an integral weighted by time, $M'_1$ does not equal $-M_1$. The phase accumulated by the combined bipolar gradient lobe is then the sum of Eqn.[7] and Eqn.[8], which is given by:

$$\phi_1 = \phi + \phi' = \gamma v(M'_1 + M_1). \quad [9]$$

Note that the phase accumulation from an applied bipolar gradient is independent of initial position and is directly proportional to the velocity. The bipolar gradient has a zero net area and has no effect on stationary tissue. Thus, without any loss of generality, G(t) can be considered a single bipolar waveform, such that the phase is simply given by Eqn. [2]:

$$\phi = \gamma M_1 \vec{v} \quad [2]$$

In a perfect experiment, a single acquisition with a bipolar gradient will provide an image whose phase represents flow in the direction of the applied gradient as given by Eqn.[2]. However, residual eddy currents, magnetic field homogeneity, and magnetic susceptibility contribute to a spatially varying non-zero phase, even for stationary tissue. This spatial phase variation is not flow-related and can be large across an image. In order to avoid this problem, two images with bipolar gradients of opposite sign (toggled bipolar gradients) are subtracted. Any non-zero phase due to stationary tissue are canceled out, leaving an image with the difference in phase accumulated in the two acquisitions. By inverting the bipolar waveform for the second acquisition, the phase of this subsequent acquisition is the negation of Eqn.[2], (i.e., $\phi_2 = -\phi_1$), and $M_{1,acq2} = -M_{1,acq1} = -M_1$. The phase difference in the subtracted image is then:

$$\Delta\phi = \phi_1 - \phi_2 = \gamma \vec{v} \Delta M_1, \qquad [10]$$

with $$\Delta M_1 = \int_0^t 2tG(t)dt \qquad [11]$$

From the phase difference equation, Eqn.[10], it is clear that if the spins reverse flow direction, i.e., $\vec{v}$ reverses sign, there is a corresponding change in the sign of $\Delta\phi$. Thus, the magnitude of a phase difference image provides a measure of the flow velocity, while the sign indicates flow direction.

The phase difference image (after subtraction) displays the value of Eqn.[10] at each pixel. The phase shift given by Eqn.[10] is proportional to velocity and the difference in the first gradient moment (Eqn.[11]). If $\Delta\phi$ exceeds $\pi$ radians or 180°, or the misrepresentation of one phase as that of another different phase, aliasing occurs, as shown in FIG. 5. For example, a phase difference of +190° is indistinguishable from a phase difference of −170° or even −530°. Thus, spins with a high velocity may be represented as having a lower velocity or spins flowing in one direction may be incorrectly represented as flowing in the opposite direction. This is the phenomenon herein referred to as velocity flow aliasing and is analogous to image warp-around.

In order to find the point of flow related aliasing, the phase shifts in Eqn.[10] are first brought to within ±180° (±$\pi$ radians). Then by dialing up the VENC value until the onset of flow related aliasing, the peak velocity can be determined as previously mentioned.

Accordingly, the present invention includes a method of identifying a stenotic vessel using MR imaging that includes performing a screening study by acquiring a first MR image having a low resolution to scan a suspected stenosis region, and then analyzing the first MR image to identify a suspected stenosis within the suspected stenosis region. This aspect of the invention next includes performing a detailed study by acquiring a second MR image having a higher resolution than the first MR image to scan the identified suspected stenosis, and then analyzing the second MR image to identify an actual stenosis.

Optionally, the invention includes an additional step of grading the actual stenosis using the second MR image. Preferably, the first MR image is acquired to provide high sensitivity to lesion detection in a blood vessel. The steps of acquiring a second MR image and analyzing the second MR image are conditioned upon identifying a suspected stenosis in the previous step of analyzing the first MR image. If none is so identified, the exam can be completed without acquiring a second time consuming image. The first MR image is acquired with a pulse sequence using flow sensitizing bi-polar gradients and initially setting a VENC value of a first moment of the flow sensitizing bi-polar gradients to a nominally low value to establish a velocity distribution greater than $2\pi$ within each voxel. When analyzing the first MR image, the detection of flow voids about a vessel is an indication of the presence of a stenosis. In order to acquire the first MR image with high phase cancellation, either a pulse sequence with bi-polar gradients to accentuate phase cancellation is used, or the voxel size is increased for greater distribution of velocity vectors, to thereby increase flow dephasing.

The invention also includes an examination method to identify a lesion in a blood vessel and grade a stenosis resulting therefrom. The examination method includes acquiring a first MR image using a gradient echo imaging pulse sequence having a flow sensitizing bi-polar gradient waveform, and detecting and localizing a suspected stenosis within the first MR image. If a stenosis is identified and localized, the examination continues with acquiring a second MR image having a higher resolution than the first MR image in a region in which the suspected stenosis is detected and localized to then grade the suspected stenosis. Conversely, if a stenosis is not detected and localized, the examination is ended without further time consuming image acquisitions.

Preferably, the second MR image is acquired with low phase cancellation and high resolution in order to isolate and grade the suspected stenosis. This is accomplished by either comparing diameters of the blood vessel along a length of the suspected stenosis, or comparing a velocity gradient along the length of the suspected stenosis.

The aforementioned methods are incorporated into an MRI apparatus that can conduct MR stenosis screening, and if necessary grade a stenotic vessel. The apparatus includes an MRI system having a plurality of gradient coils positioned about the bore of a magnet to impress a polarizing magnetic field, an RF transceiver system, and an RF switch controlled by a pulse module to transmit RF signals to an RF coil assembly to in turn acquire MR images. A computer is programmed to operate the MRI system in two modes to efficiently conduct the stenosis exam. The first mode is programmed to acquire at least one first MR image with low resolution over a relatively large region. As one skilled in the art will recognize, in some cases it may be preferable to acquire more than one first screening MR image. The first mode also allows a user to analyze the first MR image for an indication of a suspected stenosis, and receive input to either end the stenosis exam or switch to the second mode. The second mode is programmed to create a localized region of the relatively large region to target the suspect stenosis, and then acquire at least one second MR image with resolution higher than that of the at least one first MR image. Again, more than one second MR image may be acquired, for example, if there are multiple suspected stenoses located using the first MR images.

The computer of the MRI apparatus is also programmed to use a first pulse sequence for the acquisition of the first MR image. The first pulse sequence having a flow sensitizing bi-polar gradient waveform. A second pulse sequence is then used for the acquisition of the second MR image. The second pulse sequence provides less phase cancellation than the first pulse sequence. The first pulse sequence also includes a VENC value of a first moment of the flow sensitizing bi-polar gradient waveform that is set to a nominally low value, that is substantially lower than that of the second pulse sequence.

Preferably, the first MR image results in an encoded velocity distribution that is greater than $2\pi$ within each voxel. The computer is programmed to increase flow dephasing in the first MR image by either an increase in voxel size for greater distribution of the velocity vectors, or use a bi-polar gradient waveform as previously mentioned.

The invention also includes a computer readable storage medium having stored thereon a computer program having instructions which, when executed by a computer, cause the computer to acquire a first MR image of a relatively large region. The first MR image has high phase cancellation to screen a patient for possible arterial lesions. The program also causes the computer to limit an FOV to a target region within the relatively large region if a possible arterial lesion is located, and then acquire a second MR image of the targeted region. The second MR image has a resolution higher than that of the first MR image. The first MR image is acquired using either a pulse sequence with bi-polar gradients to accentuate phase cancellation, or an increased voxel size for greater distribution of velocity vectors, each to increase flow dephasing. The second MR image is acquired with low phase cancellation and high resolution in order to isolate and grade the suspected stenosis located with the first MR image. Such isolation and gradation is accomplished by either comparing diameters of the blood vessel along a length of the suspected stenosis, or comparing a velocity gradient along the length of the suspected stenosis.

The present invention has been described in terms of the preferred embodiment, and it is recognized that equivalents, alternatives, and modifications, aside from those expressly stated, are possible and within the scope of the appending claims.

What is claimed is:

1. A method of identifying a stenotic vessel using MR imaging comprising the steps of:
    performing a screening study by:
        acquiring a first MR image having a low resolution to scan a suspected stenosis region;
        analyzing the first MR image to identify a suspected stenosis within the suspected stenosis region;
    performing a detailed study by:
        acquiring a second MR image having a higher resolution than the first MR image to scan the identified suspected stenosis; and
        analyzing the second MR image to identify an actual stenosis.

2. The method of claim 1 further comprising the step of grading the actual stenosis using the second MR image.

3. The method of claim 1 wherein the first MR image acquired provides high sensitivity to lesion detection in the blood vessel.

4. The method of claim 1 wherein the steps of acquiring a second MR image and analyzing the second MR image are conditional upon identifying a suspected stenosis in the step of analyzing the first MR image.

5. The method of claim 1 further comprising the step of applying a pulse sequence with at least one flow-sensitizing bi-polar gradient.

6. The method of claim 5 further comprising the step of initially setting a velocity encoding (VENC) value of a first moment of the at least one flow-sensitizing bi-polar gradient to a nominally low value to establish a velocity distribution greater than 2p within each voxel.

7. The method of claim 1 wherein the step of analyzing the first MR image includes detecting flow voids as an indication of a suspected stenosis.

8. The method of claim 1 wherein the first MR image is acquired with high phase cancellation using at least one of:
    (1) applying a pulse sequence with bi-polar gradients to accentuate phase cancellation; and
    (2) increasing voxel size for greater distribution of velocity vectors; to thereby increase flow dephasing.

9. The method of claim 1 wherein the second MR image is acquired with low phase cancellation and high resolution in order to isolate and grade the suspected stenosis by at least one of:
    (1) comparing diameters of the blood vessel along a length of the suspected stenosis; and
    (2) comparing a velocity gradient along the length of the suspected stenosis.

10. The method of claim 1 wherein the step of acquiring a first MR image includes applying a pulse sequence with bi-polar gradients to accentuate phase cancellation and thereby increase flow dephasing.

11. The method of claim 1 wherein the step of acquiring a first MR image includes increasing voxel size for greater distribution of velocity vectors to thereby increase flow dephasing.

12. An examination method to identify a lesion in a blood vessel and grade a stenosis resulting therefrom comprising the step of:
    acquiring a first MR image using a gradient echo imaging pulse sequence having a flow sensitizing bi-polar gradient waveform;
    detecting and localizing a suspected stenosis using the first MR image;
    if a stenosis is detected and localized, acquiring a second MR image having a higher resolution than the first MR image in a region in which the suspected stenosis is detected and localized to grade the suspected stenosis; and
    if a stenosis is not detected and localized in the step detecting and localizing, ending the examination method without further MR image acquisition.

13. The method of claim 12 wherein the first MR image is a low resolution image with high sensitivity to velocity flow for detecting a lesion on a blood vessel.

14. The method of claim 13 wherein the step of detecting a lesion includes detecting velocity flow voids in the first MR image.

15. The method of claim 12 further comprising the step of increasing intra-voxel flow dephasing effects.

16. The method of claim 12 further comprising the step of applying flow sensitizing gradients in all three directions to provide insensitivity to orientation of the blood vessel.

17. The method of claim 12 wherein the first MR image is acquired with high phase cancellation to increase flow dephasing using at least one of:
    (1) applying a pulse sequence with bi-polar gradients to accentuate phase cancellation; and
    (2) increasing voxel size for greater distribution of velocity vectors.

18. The method of claim 12 wherein the second MR image is acquired to isolate and grade the suspected stenosis by at least one of:
    (1) comparing diameters of the blood vessel along a length of the suspected stenosis; and
    (2) comparing a velocity gradient along the length of the suspected stenosis.

19. An MRI apparatus to conduct MR stenosis screening, and if necessary, grade a stenotic vessel comprising:
    a magnetic resonance imaging (MRI) system having a plurality of gradient coils positioned about a bore of a magnet to impress a polarizing magnetic field and an RF transceiver system and an RF switch controlled by a pulse module to transmit RF signals to an RF coil assembly to acquire MR images; and a computer programmed to operate the MRI system in two modes to efficiently conduct a stenosis exam, the first mode programmed to:
  acquire at least one first MR image with low resolution over a relatively large region;
  allow a user to analyze the at least one first MR image for an indication of a suspected stenosis;
  receive input to either end the stenosis exam or switch to the second mode;

the second mode programmed to:
  create a localized region of the relatively large region to target the suspected stenosis; and
  acquire at least one second MR image with resolution higher than that of the at least one first MR image of the localized region.

20. The MRI apparatus of claim 19 wherein the computer is further programmed to:
  use a first pulse sequence for the acquisition of the at least one first MR image, the first pulse sequence having a flow-sensitizing bi-polar gradient waveform; and
  use a second pulse sequence for the acquisition of the at least one second MR image, the second pulse sequence providing less phase cancellation than the first pulse sequence.

21. The MRI apparatus of claim 20 wherein the first pulse sequence includes a VENC value of a first moment of the flow-sensitizing bi-polar gradient waveform set to a nominally low value.

22. The MRI apparatus of claim 21 wherein the VENC value is set substantially lower than that of the second pulse sequence.

23. The MRI apparatus of claim 19 wherein an encoded velocity distribution is greater than 2p within each voxel for the first MR image.

24. The MRI apparatus of claim 19 wherein the computer is further programmed to increase flow dephasing in the first MR image.

25. The MRI apparatus of claim 24 wherein the increase in flow dephasing is accomplished by an increase in voxel size for greater distribution of velocity vectors.

26. A computer readable storage medium having stored thereon a computer program comprising instructions which, when executed by a computer, cause the computer to:
  acquire a first MR image of a relatively large region, the first MR image having high phase cancellation to screen a patient for possible arterial lesions; and
  limit a FOV to a target region within the relatively large region if a possible arterial lesion is located, then
  acquire a second MR image of the targeted region, the second MR image having a resolution higher than that of the first MR image.

27. The computer readable storage medium of claim 26 wherein the first MR image is acquired with high phase cancellation using at least one of:
  (1) applying a pulse sequence with bi-polar gradients to accentuate phase cancellation; and
  (2) increasing voxel size for greater distribution of velocity vectors;
  to thereby increase flow dephasing.

28. The computer readable storage medium of claim 26 wherein the computer is further programmed to:
  use a first pulse sequence for the acquisition of the at least one first MR image, the first pulse sequence having a flow-sensitizing bi-polar gradient waveform; and
  use a second pulse sequence for the acquisition of the at least one second MR image, the second pulse sequence providing less phase cancellation than the first pulse sequence.

29. The computer readable storage medium of claim 26 wherein the computer is further programmed to:
  apply a pulse sequence with at least one flow-sensitizing bi-polar gradient; and
  initially set a velocity encoding (VENC) value of a first moment of the at least one flow-sensitizing bi-polar gradient to a nominally low value to establish a velocity distribution greater than 2p within each voxel.

30. The computer readable storage medium of claim 26 wherein the computer is further programmed to detect lesions by detecting velocity flow voids in the first MR image.

31. The computer readable storage medium of claim 26 wherein the computer is further programmed to acquire the second MR image with low phase cancellation and high resolution in order to isolate and grade the suspected stenosis by at least one of:
  (1) comparing diameters of the blood vessel along a length of the suspected stenosis; and
  (2) comparing a velocity gradient along the length of the suspected stenosis.

* * * * *

UNITED STATES PATENT AND TRADEMARK OFFICE
CERTIFICATE OF CORRECTION

PATENT NO. : 6,741,880 B1 Page 1 of 1
APPLICATION NO. : 09/595117
DATED : May 25, 2004
INVENTOR(S) : Foo et al.

It is certified that error appears in the above-identified patent and that said Letters Patent is hereby corrected as shown below:

On the cover page, column 1, under "Assignee:" after "General Electric Company, Schenectady, NY (US)", add -- ; Uniformed Services University of Health Sciences, Bethesda, MD (US) --.

Signed and Sealed this

Nineteenth Day of September, 2006

JON W. DUDAS
*Director of the United States Patent and Trademark Office*